United States Patent [19]

Check, III et al.

[11] Patent Number: 5,093,041
[45] Date of Patent: Mar. 3, 1992

[54] LIGHT-POLARIZING MATERIAL BASED ON ETHYLENEDIAMINE POLYACETIC ACID DERIVATIVES

[75] Inventors: Joseph A. Check, III, Massapequa; Robert L. Saxe, New York, both of N.Y.

[73] Assignee: Research Frontiers Incorporated, Woodbury, N.Y.

[21] Appl. No.: 559,727

[22] Filed: Jul. 30, 1990

[51] Int. Cl.$^5$ .......................... F21V 9/14; G02F 1/00; G02B 26/00; G02B 5/30
[52] U.S. Cl. ..................... 252/585; 252/583; 359/253; 359/296; 359/488
[58] Field of Search .................. 252/582, 585, 583; 350/395, 398, 362, 391

[56] References Cited

U.S. PATENT DOCUMENTS

| | | | |
|---|---|---|---|
| 4,680,103 | 7/1987 | Solomon, I et al. | 350/362 |
| 4,877,313 | 10/1989 | Saxe et al. | 252/585 |
| 4,895,677 | 1/1990 | Okumura et al. | 252/585 |
| 5,002,701 | 3/1991 | Saxe | 252/585 |

Primary Examiner—John S. Maples
Assistant Examiner—Philip Tucker
Attorney, Agent, or Firm—Rosenman & Colin

[57] ABSTRACT

Light-polarizing materials, and uses thereof in liquid suspensions, set suspensions and light valves.

12 Claims, No Drawings

LIGHT-POLARIZING MATERIAL BASED ON ETHYLENEDIAMINE POLYACETIC ACID DERIVATIVES

This invention relates to light-polarizing materials, to set suspensions and fluid suspensions thereof, and to light valves containing such fluid suspensions. In particular, the present invention relates to organic light-polarizing materials that are derived from organic compounds that do not have a nitrogen heteroatom, which is characteristic of prior art organic light-polarizing materials.

Light-polarizing materials, such as colloidal suspensions of herapathite and herapathite-like light-polarizing crystals, are described in U.S. Pat. Nos. 1,951,664 (Land) and 2,178,996 (Land), respectively U.S. Pat. No. 2,237,567 (Land) discloses the production of light-polarizing material in sheet form by various methods including application of a solution of iodine and an iodide to a sheet of polyvinyl alcohol which had been previously stretched to orient the molecules therein. Numerous other patents relating to light-polarizing materials, set suspensions thereof and laminated products derived therefrom and uses thereof are in the art including, for example, U.S. Pat. Nos. 2,041,138 (Land), 2,078,254 (Land), 2,168,220 (Land), 2,168,221 (Land), 2,185,018 (Sauer), 2,230,262 (Pollack), 2,246,087 (Bailey et al), 2,256,108 (Blake), 2,263,249 (Rogers), 2,306,108 (Land et al), 2,328,219 (Land), and 2,375,963 (Thomas). U.K. Patent 433,455 discloses the use of particles of purpureocobaltchloridesulphateperiodide in the formation of light-polarizing bodies. These and the other patents and prior art referred to in this specification are incorporated herein by reference thereto.

At present, important uses for laminated set suspensions of light-polarizing materials, often referred to as "sheet polarizers", include lenses for polarized sunglasses, components of the twisted nematic and other types of liquid crystal displays and filters of various types including contrast enhancement filters for use in conjunction with light emissive displays. However, the sheet polarizers thus employed are well known to be frequently subject to degradation due to high levels of heat, ultraviolet radiation and/or especially moisture.

Fluid suspensions of light-polarizing and other materials have been used in light valves, comprising a cell containing a fluid suspension of minute particles which can be oriented by an electric or magnetic field to change the transmission of light through the suspension. See for example, U.S. Pat. Nos. 3,708,219 (Forlini et al), 3,743,382 (Rosenberg), 4,078,856 (Thompson et al), 4,113,362 (Saxe et al), 4,164,365 (Saxe), 4,407,565 (Saxe), and 4,422,963 (Thompson et al).

U.S. Pat. No. 4,131,334 (Witte et al) describes a process for forming light-polarizing particles by hydrogenation of a nitrogen-containing organic compound, which is then reacted with an appropriate acid to form a salt. The salt may then be reacted, usually with iodine and an inorganic iodide, to produce stable polyiodide particles.

An object of the present invention is to provide light-polarizing materials that have high stability with respect to ultraviolet radiation, elevated temperatures and high levels of moisture.

Polyhalides, including polyiodides, have been known for quite some time. A polyiodide is a complex of iodine atoms and an inorganic or organic matrix. Godina et al discuss polyiodides and other polyhalides in detail in J. Gen. Chem. USSR, 20, (1950), pages 1005-1016. Among the known polyiodides is the light-polarizing crystalline material, herapathite, which is formed by reaction of quinine bisulfate, iodine and HI. Salts of other members of the quinine alkaloid family also form light-polarizing polyiodides by reaction with iodine and HI, such as cinchonidine bisulfate. In these materials, the elemental iodine combines with the alkaloid acid salt in the form of the polyiodide anion, which has been variously described as $I_3^-$ by Godina et al and as $I_5^-$ by Teitelbaum et al, JACS, 100 (1978) pages 3215-3217. Godina et al show that the polyiodide anion is formed by reaction between iodine and HI, e.g.

$$I_2 + HI = H^+ I_3^- \qquad (1)$$

Likewise, the $I_5^-$ polyiodide anion would be formed by the reaction

$$2I_2 + HI = H^+ I_5^- \qquad (2)$$

Godina et al explain that light-polarizing polyiodides comprise the polyiodide anion and the acid salt of quinine and the like as the cation. However, polyiodides can also be formed without any apparent cation being present, such as the starch-iodine complex and the stretched or oriented polyvinyl alcohol-iodine complex. Teitelbaum et al report that the starch-iodine complex contains adsorbed iodine in the form of chains of iodine within the amylase component of starch, the chains being made up of $I_5^-$ polyiodide anions as the dominant species. Godina et al theorize that herapathite, starch-iodine and oriented PVA-iodine complex are "adsorbing polyiodides" in which molecular iodine is adsorbed in layers on the polyiodide chains.

The light-polarizing material of the present invention is a complex that does not contain the nitrogen heteroatom characteristic of prior art organic light polarizing materials. This complex is obtained by reacting (i) elemental iodine, (ii) a hydrohalide acid and/or an ammonium or alkali metal or alkaline earth metal halide and (iii) an ethylene diamine derivative of formula I below. This complex contains adsorbed molecular iodine. When HI or an iodide is used, we believe that the complex also contains the polyiodide anion, $I_x^-$, where x is 3 or 5, since Godina et al and Teitelbaum et al both report that the polyiodide anion is formed by reaction between (i) elemental iodine and (ii) an iodide. Moreover, Godina et al report that crystals containing adsorbed molecular iodine and the polyiodide anion are light-polarizing.

In the Examples that follow, light polarizing materials are prepared by reacting a compound I with iodine and an iodide, bromide or chloride. In such cases, we believe that the respective anions would be

-I-I-I-I-I-

-I-I-B̄r-I-I

-I-I-C̄l-I-I using the structure elucidated by Teitelbaum et al as a model.

Godina et al report that light-polarizing complexes containing adsorbed molecular iodine cannot be defined stoichiometrically by structural formula. Hence, the light-polarizing material of the present invention is defined in product-by-process format.

Compounds I that are useful in forming the light-polarizing materials of the invention are compounds having the formula:

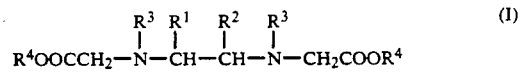

wherein $R^1$ and $R^2$ are independently hydrogen or lower alkyl, $R^3$ is hydrogen or $-CH_2COOR^4$, and each $R^4$ is independently hydrogen or M/n, where M is an alkali metal or alkaline earth metal and n is the valence of M.

When $R^1$ and/or $R^2$ is lower alkyl, the lower alkyl may be straight or branched chain alkyl, such as methyl, ethyl, propyl, isopropyl, butyl, isobutyl, t-butyl and the like. Usually, the lower alkyl will have from 1 to about 6 carbon atoms, preferably from 1 to about 4 carbon atoms.

Compounds I are known per se or may be isomers, homologues or analogs of known compounds and may be prepared analogously to such known compounds.

Since the free acid form of compounds I, such as ethylene diamine tetraacetic acid, ethylene diamine diacetic acid, 1,2-diaminopropyl tetraacetic acid (i.e. $R^1$ is methyl, $R^2$ is hydrogen and each $R^3$ is $-CH_2COOH$) and the like, have limited water solubility, compound I will either be used in the form of a water-soluble alkali metal and/or alkaline earth metal salt thereof, or the water-soluble salt can be formed in situ during the formation of the light-polarizing material. Useful compounds I include ethylene diamine tetraacetic acid or the disodium, dipotassium, tetrasodium, tetrapotassium or disodium magnesium salts thereof, ethylene diamine diacetic acid or the mono- or di- sodium or mono- or di-potassium salts thereof, 1,2-diaminopropyl tetraacetic acid or the disodium, dipotassium, tetrasodium or tetrapotassium salts thereof and the like.

The light-polarizing materials of this invention are formed by reacting a compound of formula I with elemental iodine and a hydrohalide acid and/or an ammonium, alkali metal or alkaline earth metal halide, in a suitable solvent, such as water. See U.S. Pat. Nos. 1,951,661, 2,176,516 and 2,289,712. The halide is usually an iodide, but can also be a bromide or chloride. Preferably, the reaction to form the polyhalide takes place in the presence of a protective colloid, such as nitrocellulose or a copolymer as disclosed in U.S. Pat. No. 4,164,365, issued Aug. 14, 1979. It is presently preferred to provide compound I in a first solution and a mixture of iodine and ammonium or alkali metal or alkaline earth metal halide in a second solution, but, if desired, the halide can be in either or both of the solutions. The solutions are then mixed together, and the polyhalides are readily formed even at room temperature. Light-polarizing polyhalide crystals are then recovered by any suitable technique, such as by filtering and the like.

Heretofore, organic light-polarizing materials have been made only by reacting molecular iodine and an iodide or the like with organic precursor compounds having at least one heterocyclic ring containing a nitrogen heteroatom, such as quinine bisulfate, dihydrocinchonidine bisulfate and quinaldic acid anhydride and the precursor compounds described in U.S. Pat. No. 4,877,313. Surprisingly, the present invention provides an organic light-polarizing material obtained from the precursor compound (I), which does not contain a nitrogen heteroatom.

For use in a light valve, the polyhalide particles are suspended in a liquid suspending medium. As is known, the liquid suspending medium may be virtually any electrically resistive liquid so long as it suspends the particles and dissolves the polymeric stabilizer. Preferably, the liquid suspending medium has a relatively high electrical resistivity and low vapor pressure, and does not degrade or attack the particles or other components of the suspension. See e.g. U.S. Pat. Nos. 4,270,841 and 4,407,565 to Saxe.

For use in set suspensions, the polyhalide particles are dispersed or distributed throughout a sheet formed of suitable film-forming material, such as cellulose acetate or polyvinylalcohol or the like. See e.g. U.S. Pat. Nos. 2,178,996 and 2,041,138.

EXAMPLES 1-3

Approximately 2 g. of disodium ethylene diamine tetraacetic acid was dissolved in 5 g. of water and that solution was then mixed with 5 g. of a solution of water in which 0.8 g of iodine and 1 g. of calcium iodide were dissolved. Blue-colored light-polarizing crystals formed readily. The same procedure was followed and similar results observed using dipotassium and disodium magnesium ethylene diamine tetraacetic acid, respectively, in place of disodium ethylene diamine tetraacetic acid.

EXAMPLES 4-5

Approximately 0.5 g of ethylene diamine diacetic acid was dissolved in 5 g. of 2% aqueous sodium hydroxide and that solution was then mixed with 5 g. of a solution of water in which 0.8 g of iodine and 1 g. of calcium iodide were dissolved. Blue-colored light-polarizing crystals formed readily. The same procedure was followed and similar results observed using 1,2-diaminopropyl tetraacetic acid in place of ethylene diamine diacetic acid.

Comparative Examples 6-12

Comparative Examples 6-12 used compounds 6-12 below, respectively
6—1,6-Hexanediamine tetraacetic acid
7—Nitrilotriacetic acid
8—Ethylene (oxyethylenenitrilo)tetraacetic acid (EGTA)
9—Methyliminodiacetic acid
10—Iminodiacetic acid
11—10-(2-Hydroxyethyl)ethylene diamine triacetic acid
12— N-(2-Hydroxyethyl)iminodiacetic acid.

Approximately 0.5 g of compound 6 was dissolved in 5 g. of 2% aqueous sodium hydroxide and that solution was then mixed with 5 g. of a solution of water in which iodine and calcium iodide were dissolved according to the same amounts and procedures as in examples 4-5. No light-polarizing crystals were produced. The same procedure was followed and similar failure to produce polarizing crystals observed using compounds 7-12 in place of compound 6.

The failure to form light-polarizing crystals in comparative example 6, wherein 1,6-hexanediamine tetraacetic acid was used, is in sharp contrast to the success described above where EDTA was used under similar reaction conditions. The greater distance between the nitrogen atoms is the only difference that could account for the failure described in Examples 6 and 8.

The failure to form polarizing crystals in comparative Examples 7, 9, 10 and 12 can be possibly explained by the fact that these compounds contain only one nitrogen atom. It appears that having two nitrogen atoms separated by no more than two carbon atoms is essential to the formation of light-polarizing crystals.

All of the compounds I used in the present invention are known to form metal salts and/or to be metal-chelating compounds, such as shown below, wherein $R^4$ is calcium: Accordingly, one possible explanation for the formation of the light-polarizing materials of this invention is that when the compounds I are reacted with iodine and a halide, the halide and iodine enter into the reaction in an ionic form. For example, if the halide is calcium iodide, $CaI_2$, iodine may enter the reaction as $Ca^{+2}(I_x)_2^-$, with the positively charged calcium ion being chelated by the compound I and the $(I_x)^-$ anion being bonded to the positive calcium ion, thereby forming a polyiodide crystal. While this explanation seems reasonable, it is not intended that this application be bound by this theory.

Liquid suspensions of the polyhalide particles of this invention can be easily prepared by utilizing a procedure somewhat similar to that for preparing liquid suspensions of dihydrocinchonidine sulfate polyiodide described in Example 2 of U.S. Pat. No. 4,131,334 and in Example 1 of U.S. Pat. No. 4,407,565, but with compound I of the present invention substituted for dihydrocinchonidine sulfate and the quantities of the reactants adjusted as, for example, given in the aforesaid examples.

EXAMPLE 13

A. Preparation of Dipotassium Ethylene Diamine Tetraacetic Acid Polyiodide - Nitrocellulose Complex Solution A was prepared by dissolving 3 g. of dipotassium ethylenediamine tetraacetic acid in 15 g. of a mixed solvent comprising 5 g. of water and 10 g. of 2-ethoxyethanol.

Solution B was a 33⅓% solution of nitrocellulose in 2-ethoxyethanol. The nitrocellulose is a mixed viscosity (18-25 cps and 15-20 sec) type.

Solution A and 22 g. of solution B were mixed to form solution C.

Solution D was prepared by dissolving 0.48 g. of calcium iodide hexahydrate in 10 g. of 2 ethoxyethanol and then adding 1.4 g. of $I_2$ and 20 g of tricresylphosphate (TCP) and shaking for 10 minutes.

Solution C was combined with solution D with vigorous mixing in a Waring blender while stirring with a polyethylene spatula. After stirring for two minutes the wet paste was spread as an 8 ml film on a glass plate and allowed to dry overnight. The light-polarizing crystals formed as the paste dried.

B. Preparation of the Liquid Suspension

The dried paste was scraped off the glass plate and dispersed into 150 g. of isopentyl acetate (IPA) and well shaken so as to disperse the paste to form a liquid suspension. The suspension is then ultrasonically agitated for 10 hours and centrifuged at 11,000 RPM for one hour. The sediment is then resuspended in IPA and an effective amount of a suitable polymer solution added thereto, e.g. 10-15 g. of a 15% solution of a 96.75%/3.25% copolymer of neopentyl acrylate/methylol acrylamide dissolved in neopentyl neopentanoate may be added. This new suspension is placed in a vacuum apparatus for approximately five hours to evaporate off nearly all of the IPA. Part of any other solvent present that does not have too high a boiling point may also evaporate. The suspension is then diluted to the extent desired with Halocarbon Oil type 0.8/100 (manufactured by Halocarbon Products, Hackensack, N.J.) and any other desired solvents, such as neopentyl neopentanoate, to provide the wanted off-state optical density and response time. Additional polymer may be added.

Liquid suspensions of the type described above can be used in light valves which utilize an AC electric field to orient the particles in said suspensions to change and/or control the transmission of light through the suspension. Such light valves can be used, for example, as variable transmission windows, filters, mirrors, and eyeglasses, and as electronic alphanumeric and graphic image displays.

By modifying the composition of the suspension, however, it is possible to produce what is known in the prior art as a set suspension, rather than a fluid suspension or liquid suspension usable in a light valve as described above. A set suspension of the particles of the present invention would comprise, for example, a light-polarizing sheet or film in which said particles would be incorporated along with other materials.

There are many processes known in the art for producing light-polarizing sheets and films. For example, U.S. Pat. No. 2,178,996 discloses a process for forming certain light-polarizing particles, mixing said particles into a dispersion medium which may include cellulose acetate, and subjecting the dispersion of particles to flow or extrusion or stretch, or rolling, so that the needle axis of the dispersed polarizing crystals may be oriented to substantial parallelism and a thin, sheet-like polarizing body produced. U.S. Pat. No. 2,041,138 discloses that polarizing bodies may preferably be made in the form of a relatively thin sheet or film comprising the suspending medium and the minute particles dispersed therein. If desired, the polarizing body may itself be permanently or detachably fixed to a suitable support, preferably transparent, as for example, to a plate of glass or to a sheet of celluloid. Such a support may be desirable with conditions where it is found that the polarizing body itself may require some form of protection. It also discloses the use of asymmetric particles, the flowing of the medium that includes said particles past an edge, and retaining said particles in an oriented position by setting or hardening said medium.

U.S. Pat. No. 2,168,220 discloses information relating to polarizing material sold under the trade name "Polaroid". Use of plasticizers, adhesives and various types of laminations and methods for forming said laminations are disclosed.

Numerous types of polarizing films and uses for polarizers are disclosed in U.S. Pat. No. 2,246,087 including, for example, use in windshields, windows, eyeglasses, goggles, sunglasses, camera lenses, microscopes, mirrors and in connection with three dimensional movies.

A process for transferring light-polarizing films from one support to another and various materials used in connection therewith are disclosed in U.S. Pat. No. 2,256,108.

The information available from any of the aforesaid patents and from numerous other patents and other sources known in the art can be used to make light-polarizing set suspensions, films and sheets which include particles oriented in substantial parallelism, and light-polarizing bodies and products made therefrom.

However, many light polarizers in commercial use today do not incorporate films or sheets having solid discrete particles oriented in parallel therein, but rather use a sheet of polyvinyl alcohol polyiodide which has its optic axis in the plane of the sheet and which transmits with substantially no absorption only light vibrating substantially perpendicularly to its optic axis, as described in U.S. Pat. Nos. 2,237,567 and 2,375,963 and other sources known in the art. The commercially available polarizers are known to be susceptible to degradation when subjected for prolonged periods to harsh environmental conditions such as high temperatures, high humidity, ultraviolet radiation and especially combinations of such conditions.

Despite the problems of commercially available sheet polarizers with respect to environmental degradation, it may be preferable or desirable from a manufacturing viewpoint to react a stretched sheet of polymer with dyes or stains or with iodine and an iodide to form a light-polarizing complex, rather than to use a plurality of individual polarizing crystals as previously described. To this end, useful embodiments of the present invention also include compounds comprising compounds of this invention, each molecule of which as attached thereto a polymerizable unsaturated group.

However, the polarizers made from set suspensions of the particles and other materials of the present invention will be stable to high levels of heat and ultraviolet radiation and will tolerate water excellently. Accordingly, the present invention makes possible a substantial improvement in the quality of light-polarizing bodies and products incorporating such materials.

Although specific embodiments of the invention have been described, it will be appreciated that many modifications thereon may be made by one skilled in the art, which fall within the spirit and scope of this invention.

We claim:

1. A light-polarizing material containing adsorbed iodine, comprising a complex obtained by reacting (i) elemental iodine, (ii) a hydrohalide acid and/or an ammonium or alkali metal or alkaline earth metal halide and (iii) a compound having the formula:

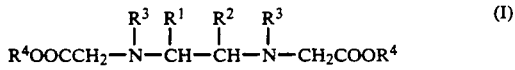

$$\begin{array}{cccc} R^3 & R^1 & R^2 & R^3 \\ | & | & | & | \\ R^4OOCCH_2-N-CH-CH-N-CH_2COOR^4 \end{array} \quad (I)$$

wherein $R^1$ and $R^2$ are independently hydrogen or lower alkyl, $R^3$ is hydrogen or $-CH_2COOR^4$, and each $R^4$ is independently hydrogen or M/n, where M is an alkali metal or alkaline earth metal and n is the valence of M.

2. The light-polarizing material according to claim 1, wherein said halide of said hydrohalide acid and/or said ammonium or alkali metal or alkaline earth metal halide is chloride, bromide or iodide.

3. The light-polarizing material according to claim 1, wherein said compound is ethylene diamine tetraacetic acid or the disodium, dipotassium, tetrasodium, tetrapotassium or disodium magnesium salts thereof, ethylene diamine diacetic acid or the mono- or di- sodium or mono- or di- potassium salts thereof, or 1,2-diaminopropyl tetraacetic acid or the disodium, dipotassium, tetrasodium or tetrapotassium salts thereof.

4. A liquid suspension for a light valve, comprising an electrically resistive liquid suspending medium, a plurality of small, anisometrically shaped particles of the light-polarizing material of claim 1 dispersed therein and at least one dispersing material dissolved therein for dispersing said particles in said suspension.

5. A liquid suspension according to claim 4, wherein said halide of said hydrohalide acid and/or said ammonium or alkali metal or alkaline earth metal halide is chloride, bromide or iodide.

6. The liquid suspension according to claim 4, wherein said compound is ethylene diamine tetraacetic acid or the disodium, dipotassium, tetrasodium, tetrapotassium or disodium magnesium salts thereof, ethylene diamine diacetic acid or the mono- or di- sodium or mono- or di- potassium salts thereof, or 1,2-diaminopropyl tetraacetic acid or the disodium, dipotassium, tetrasodium or tetrapotassium salts thereof.

7. A light-polarizing body, comprising a plurality of particles of the light-polarizing material according to claim 1, dispersed in a carrier, the polarizing axis of said particles being oriented and immovably retained by said carrier in substantial parallelism.

8. The light-polarizing body according to claim 7, wherein said halide of said hydrohalide acid and/or said ammonium or alkali metal or alkaline earth metal halide is chloride, bromide or iodide.

9. The light-polarizing body according to claim 7, wherein said compound is ethylene diamine tetraacetic acid or the disodium, dipotassium, tetrasodium, tetrapotassium or disodium magnesium salts thereof, ethylene diamine diacetic acid or the mono- or di- sodium or mono- or di- potassium salts thereof, or 1,2-diaminopropyl tetraacetic acid or the disodium, dipotassium, tetrasodium or tetrapotassium salts thereof.

10. In a light valve, comprising a cell containing a suspension of light-polarizing particles in a liquid suspending medium, the improvement wherein said light-polarizing particles are particles of the light-polarizing material according to claim 1.

11. The light valve according to claim 10, wherein said halide of said hydrohalide acid and/or said ammonium or alkali metal or alkaline earth metal halide is chloride, bromide or iodide.

12. The light valve according to claim 10, wherein said compound is ethylene diamine tetraacetic acid or the disodium, dipotassium, tetrasodium, tetrapotassium or disodium magnesium salts thereof, ethylene diamine diacetic acid or the mono- or di- sodium or mono- or di- potassium salts thereof, or 1,2-diaminopropyl tetraacetic acid or the disodium, dipotassium, tetrasodium or tetrapotassium salts thereof.

* * * * *